US011278317B2

(12) United States Patent
Baril et al.

(10) Patent No.: US 11,278,317 B2
(45) Date of Patent: Mar. 22, 2022

(54) SURGICAL ACCESS DEVICES AND SYSTEMS INCLUDING SMOKE EVACUATION

(71) Applicant: COVIDIEN LP, Mansfield, MA (US)

(72) Inventors: Jacob C. Baril, Norwalk, CT (US); Roy J. Pilletere, North Haven, CT (US); Matthew A. Dinino, Newington, CT (US); Justin J. Thomas, New Haven, CT (US); Saumya Banerjee, Hamden, CT (US)

(73) Assignee: Covidien LP, Mansfield, MA (US)

( * ) Notice: Subject to any disclaimer, the term of this patent is extended or adjusted under 35 U.S.C. 154(b) by 281 days.

(21) Appl. No.: 16/553,516

(22) Filed: Aug. 28, 2019

(65) Prior Publication Data

US 2021/0059715 A1  Mar. 4, 2021

(51) Int. Cl.
*A61B 17/34* (2006.01)
*A61B 17/00* (2006.01)

(52) U.S. Cl.
CPC .... *A61B 17/3423* (2013.01); *A61B 17/00234* (2013.01); *A61B 2017/345* (2013.01); *A61B 2218/008* (2013.01)

(58) Field of Classification Search
CPC .......... A61B 17/3423; A61B 17/00234; A61B 2218/008; A61B 2017/345; A61B 2017/3425; A61B 2017/3427; A61B 2017/3429; A61M 39/0247; A61M 39/02; A61M 2039/0279; A61M 2039/0626; A61M 2039/0297; A61M 2039/0282; A61M 2039/0276

USPC .......... 128/856; 604/332, 334, 338; 600/208
See application file for complete search history.

(56) References Cited

U.S. PATENT DOCUMENTS

| 5,578,000 | A | 11/1996 | Greff |
| 5,906,577 | A * | 5/1999 | Beane ................. A61B 17/3431 600/207 |
| 5,941,873 | A | 8/1999 | Korenfeld |
| 6,033,362 | A | 3/2000 | Cohn |
| 6,544,210 | B1 | 4/2003 | Trudel et al. |
| 7,789,946 | B2 | 9/2010 | Schultz et al. |
| 7,901,353 | B2 | 3/2011 | Vayser et al. |
| 8,641,608 | B2 * | 2/2014 | Voegele ............. A61B 17/3423 600/201 |
| 9,084,594 | B2 * | 7/2015 | Suh ..................... A61B 17/0218 |
| 9,320,861 | B2 * | 4/2016 | Fischvogt ........... A61M 13/003 |

(Continued)

*Primary Examiner* — Tan-Uyen T Ho
*Assistant Examiner* — Bridget E. Rabaglia
(74) *Attorney, Agent, or Firm* — Carter, DeLuca & Farrell LLP

(57) ABSTRACT

A surgical access system includes an access device and a distal smoke evacuator. The access device includes a proximal rim configured for positioning on an external side of an opening in tissue, a distal rim configured for positioning on an internal side of an opening in tissue, and a body interconnecting the proximal and distal rims. The body is configured to extend through an opening in tissue and defines a passageway extending therethrough for insertion of a surgical instrument through the opening in tissue into an internal surgical site. The distal smoke evacuator is integrated into or coupled to the distal rim. The distal smoke evacuator includes a tube ring adapted to connect to a source of suction to evacuate smoke circumferentially about an internal side of an opening in tissue.

18 Claims, 6 Drawing Sheets

(56) References Cited

U.S. PATENT DOCUMENTS

| | | |
|---|---|---|
| 9,427,288 B1 | 8/2016 | Chenger et al. |
| 10,076,358 B2 | 9/2018 | Zergiebel et al. |
| 2005/0054993 A1 | 3/2005 | Falahee |
| 2006/0247673 A1 | 11/2006 | Voegele et al. |
| 2010/0312066 A1* | 12/2010 | Cropper ............ A61B 17/3423 600/207 |
| 2012/0089093 A1 | 4/2012 | Trusty |
| 2013/0184536 A1 | 7/2013 | Shibley et al. |
| 2014/0330285 A1 | 11/2014 | Rosenblatt et al. |
| 2016/0158468 A1 | 6/2016 | Tang et al. |
| 2017/0049427 A1 | 2/2017 | Do et al. |
| 2017/0325657 A1 | 11/2017 | Prior |
| 2018/0008250 A1 | 1/2018 | Joseph |
| 2018/0049771 A1 | 2/2018 | Rhemrev-Pieters |

* cited by examiner

SURGICAL ACCESS DEVICES AND SYSTEMS INCLUDING SMOKE EVACUATION

FIELD

The present disclosure relates to tissue specimen removal and, more particularly, to surgical access devices and systems including one or more smoke evacuation features to facilitate tissue specimen removal procedures and other surgical procedures.

BACKGROUND

In minimally-invasive surgical procedures, operations are carried out within an internal body cavity through small entrance openings in the body. The entrance openings may be natural passageways of the body or may be surgically created, for example, by making a small incision into which an access device is inserted.

Minimally-invasive surgical procedures may be used for partial or total removal of tissue from an internal body cavity. However, the restricted access provided by minimally-invasive openings (natural passageways and/or surgically created openings) presents challenges with respect to maneuverability and visualization. The restricted access also presents challenges when large tissue specimens are required to be removed. As such, tissue specimens that are deemed too large for intact removal may be broken down into a plurality of smaller pieces or otherwise modified to facilitate removal from the internal body cavity.

SUMMARY

As used herein, the term "distal" refers to the portion that is described which is further from a user, while the term "proximal" refers to the portion that is being described which is closer to a user. The terms "generally," "substantially," and the like are meant to encompass industry-accepted tolerance variations including, for example, manufacturing, material, environment, and/or use tolerances. Further, any or all of the aspects described herein, to the extent consistent, may be used in conjunction with any or all of the other aspects described herein.

Provided in accordance with aspects of the present disclosure is a surgical access system including an access device and a distal smoke evacuator. The access device includes a proximal rim configured for positioning on an external side of an opening in tissue, a distal rim configured for positioning on an internal side of an opening in tissue, and a body interconnecting the proximal and distal rims. The body is configured to extend through an opening in tissue and defines a passageway extending therethrough for insertion of a surgical instrument through the opening in tissue into an internal surgical site. The distal smoke evacuator is integrated into or coupled to the distal rim. The distal smoke evacuator includes a tube ring adapted to connect to a source of suction to evacuate smoke circumferentially about an internal side of an opening in tissue.

In an aspect of the present disclosure, the tube ring defines an internal lumen and a plurality of apertures communicating with the internal lumen. In such aspects, the distal smoke evacuator is configured to evacuate smoke through the plurality of apertures into the internal lumen. The plurality of apertures may be defined on a distally-facing side of the tube ring and/or may define different diameters, e.g., to provide substantially equal smoke evacuation about the tube ring.

In another aspect of the present disclosure, distal smoke evacuator further includes a connector and tubing. The connector is configured to fluidly couple to the tubing to enable smoke evacuation from tube ring, through the connector, to the tubing.

In another aspect of the present disclosure, the distal smoke evacuator further includes a plurality of fingers extending proximally from the tube ring. Each finger of the plurality of fingers defines an open end and a lumen communicating with an internal lumen of the tube ring. The distal smoke evacuator is configured to evacuate smoke through the open ends of the fingers and into the internal lumen. In such aspects, the open ends of the fingers may be proximally-facing.

In still another aspect of the present disclosure, the tube ring defines the distal rim of the access device. Alternatively, the tube ring is releasably engaged with the distal rim of the access device.

In yet another aspect of the present disclosure, the distal smoke evacuator includes a plurality of clips engaged with the tube ring and configured to releasably engage the distal rim to thereby releasably engage the tube ring with the distal rim.

In still yet another aspect of the present disclosure, the surgical access system further includes a proximal smoke evacuator configured to engage the proximal rim of the access device. The proximal smoke evacuator is configured to evacuate smoke circumferentially about an external side of an opening in tissue. In aspects, the proximal smoke evacuator includes a tissue guard body. Additionally or alternatively, the proximal smoke evacuator includes a lip configured to releasably engage an overhang defined by the proximal rim to releasably engage the proximal smoke evacuator with the proximal rim within the passageway.

In another aspect of the present disclosure, the surgical access system further includes smoke evacuation tubing assembly including a first tubing coupled to the proximal smoke evacuator, a second tubing coupled to the distal smoke evacuator, a connector connecting the first and second tubings, and an outflow tubing connected to the connector. The outflow tubing is adapted to connect to a source of suction for evacuating smoke through proximal and distal smoke evacuators via the first and second tubings, respectively.

Another surgical access system provided in accordance with the present disclosure includes an access device, a distal smoke evacuator, and tubing. The access device includes a proximal portion configured for positioning on an external side of an opening in tissue, a distal portion configured for positioning on an internal side of an opening in tissue, and a body portion interconnecting the proximal and distal portions. The body portion is configured to extend through an opening in tissue and defines a passageway extending therethrough for insertion of a surgical instrument through the opening in tissue into an internal surgical site. The distal smoke evacuator is disposed at the distal portion of the access device and includes a tube ring defining an internal lumen and a plurality of fluid paths in communication with the internal lumen. The tubing is coupled to the distal smoke evacuator in fluid communication with the internal lumen and is adapted to connect to a source of suction to evacuate smoke from an internal side of an opening in tissue.

In an aspect of the present disclosure, the tube ring defines a distal rim of the access device. Alternatively, the access device includes a distal rim disposed at the distal portion thereof and tube ring is releasably engaged with the distal rim.

In another aspect of the present disclosure, the tube ring defines a plurality of apertures defining the plurality of fluid paths.

In another aspect of the present disclosure, the tube ring includes a plurality of fingers extending proximally from the tube ring. Each finger of the plurality of fingers defines an open end and a lumen. The open ends and lumens cooperate to define the plurality of fluid paths.

In still yet another aspect of the present disclosure, the surgical access system further includes a proximal smoke evacuator configured to engage the proximal portion of the access device. In such aspects, the tubing may further be configured to connect to the proximal smoke evacuator to evacuate smoke from an external side of an opening in tissue.

BRIEF DESCRIPTION OF THE DRAWINGS

The above and other aspects and features of the present disclosure will become more apparent in light of the following detailed description when taken in conjunction with the accompanying drawings wherein like reference numerals identify similar or identical elements.

DETAILED DESCRIPTION

Figure 1:
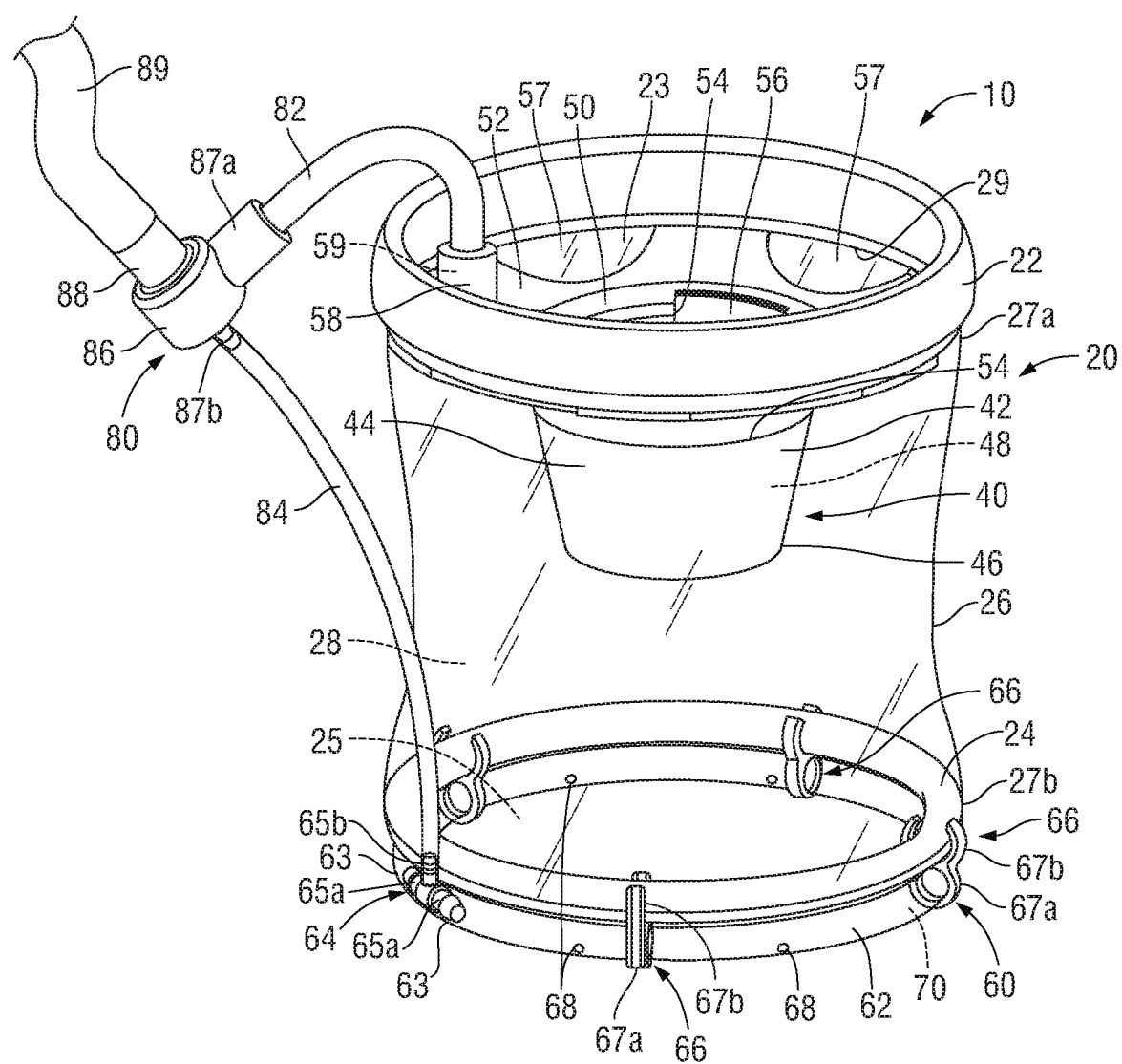
FIG. 1 is a perspective view of a surgical access system provided in accordance with the present disclosure including a surgical access device and proximal and distal smoke evacuators.
Figure 2:
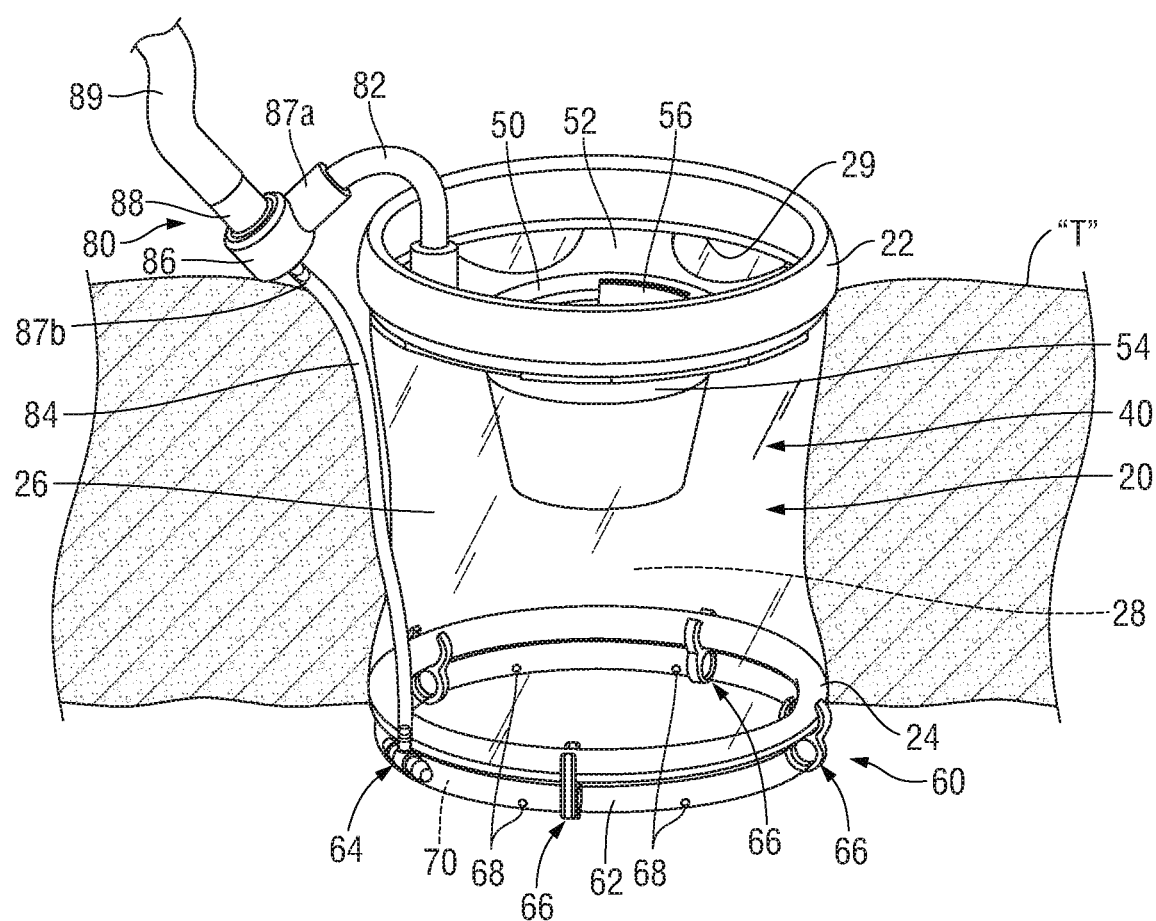
FIG. 2 is a partial cross-sectional, partial perspective view of the surgical access system of FIG. 1 positioned within an opening in tissue.
Figure 3:
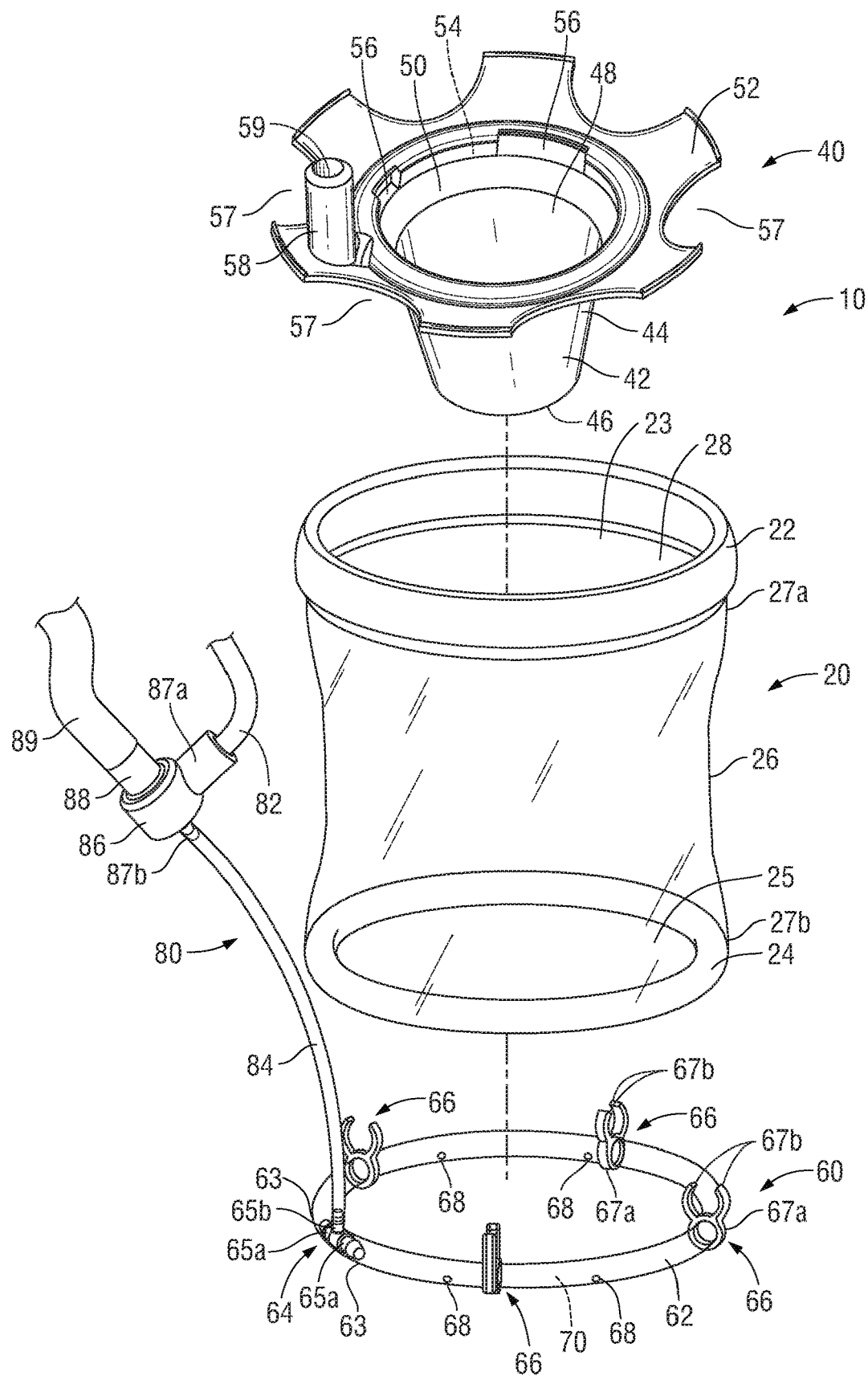
FIG. 3 is an exploded, perspective view of the surgical access system of FIG. 1.

Turning to FIGS. 1-3, a surgical access system provided in accordance with the present disclosure is shown generally identified by reference numeral 10. Surgical access system 10 includes a surgical access device 20, a proximal smoke evacuator 40, a distal smoke evacuator 60, and a smoke evacuation tubing assembly 80.

Surgical access device 20 may be configured as a tissue retractor (as shown), an access port, or other suitable access device configured for positioning within an opening in tissue "T," e.g., a surgical incision or a naturally-occurring orifice, to provide access therethrough into an internal surgical site. Access device 20 includes a proximal rim 22 configured for positioning on an external side of the opening in tissue "T," a distal rim 24 configured for positioning on an internal side of the opening in tissue "T," and a body 26 extending between proximal and distal rims 22, 24, respectively. Body 26 is configured to extend through the opening in tissue "T" and defines a passageway 28 extending longitudinally therethrough to permit access to an internal surgical site through the opening in tissue "T."

Proximal rim 22 is configured as a generally circular band defining a central opening 23 that communicates with passageway 28 of body 26. Proximal rim 22 may be formed from a resiliently flexible material, e.g., an elastomer, and, in embodiments, is configured to be rolled distally about body 26 to wind body 26 thereabout, thereby tensioning body 26 and retracting tissue "T." Proximal rim 22, in embodiments, defines an asymmetric cross-sectional configuration in at least one plane. For example, proximal rim 22 may define a crescent moon-shaped cross-sectional configuration wherein the concave side thereof faces radially inwardly. This asymmetric configuration facilitates retention of proximal rim 22 in position after each successive roll (and/or half-roll) of proximal rim 22 distally about body 26 to wind body 26 thereabout and retract tissue "T."

Continuing with reference to FIGS. 1-3, distal rim 24 is configured as a generally circular ring defining a central opening 25 that communicates with passageway 28 of body 26. Distal rim 24 may be formed from a resiliently flexible material, e.g., an elastomer, to facilitate collapse of distal rim 24 for insertion through the opening in tissue "T" and resilient return upon full insertion. Distal rim 24 may define a circular-shaped cross-sectional configuration.

Body 26 of access device 20, as noted above, extends between proximal and distal rims 22, 24, respectively, and is configured to extend through the opening in tissue "T" to permit access to an internal surgical site via the opening in tissue "T." Body 26 defines a generally tubular configuration and may be formed from any suitable material, e.g., nylon, urethane, ripstop nylon or latex, capable of forming a flexible membrane. Body 26 may be welded, at proximal end portion 27a thereof, to proximal rim 22 and at distal end portion 27b thereof to distal rim 24. Alternatively, body 26 may be attached to proximal and distal rims 22, 24, respectively, in any other suitable manner or manners. Regardless of the particular manner(s) of attachment, proximal rim 22 and body 26 cooperate to define an inwardly-extending overhang 29 therebetween that extends annularly about passageway 28.

Referring still to FIGS. 1-3, proximal smoke evacuator 40 is configured as a tissue guard incorporating smoke evacuation, although other suitable proximal smoke evacuators are also contemplated. Proximal smoke evacuator 40 is formed as a single piece of material, e.g., polyethylene, or polycarbonate, of suitable configuration to maintain its shape when positioned within an opening in tissue "T" and engaged within access device 20 while providing sufficient resilient flexibility to permit manipulation for insertion into an opening in tissue "T" and engagement within access device 20. Further, the configuration of proximal smoke evacuator 40 is selected such that proximal smoke evacuator 40 is configured to withstand cutting and puncturing by surgical knives, scalpels, pencils, and the like, thereby protecting surrounding tissue "T" and/or access device 20 from being cut or punctured. Proximal smoke evacuator 40 may additionally or alternatively be configured to inhibit transfer of thermal and/or electrical energy therethrough to protect surrounding tissue "T" and/or access device 20 from thermal and/or electrical energy.

Proximal smoke evacuator 40 includes a body 42 defining an open proximal end 44, an open distal end 46, and a lumen 48 extending therethrough between open proximal and distal ends 44, 46, respectively. Lumen 48 is configured to receive one or more surgical instruments (not shown) therethrough.

Proximal smoke evacuator 40 further includes a collar 50 disposed about open proximal end 44 of body 42 and a lip 52 extending radially outwardly from open proximal end 44 of body 42 and lumen 48. Collar 50 defines a channel 54 on an outwardly-facing side thereof. Channel 54 extends annularly about the outer circumference of collar 50 and is disposed between open proximal end 44 of body 42 and lip 52. Channel 54 may define a semi-circular cross-sectional configuration or any other suitable cross-sectional configuration and is configured to cooperate with body 26 of access device 20 to enclose a fluid flow path extending circumferentially about proximal smoke evacuator 40. Collar 50 further includes a plurality of slots 56 spaced-apart about the circumference thereof. Slots 56 are defined fully through collar 50 to establish fluid communication between channel 54, disposed on the outwardly-facing side of proximal smoke evacuator 40, and lumen 48, disposed on the inwardly-facing side of proximal smoke evacuator 40, at a plurality of radial positions about proximal smoke evacuator 40. A plurality of spaced-apart cut-outs 57 are defined about the outer circumference of lip 52. Lip 52 is configured for snap-fit engagement within inwardly-extending overhang 29 of access device 20 to releasably engage proximal smoke evacuator 40 therein.

Collar 50 of proximal smoke evacuator 40 additionally includes a connection port 58 extending proximally from lip 52. Connection port 58 defines a port lumen 59 therethrough that is disposed in fluid communication with channel 54. Connection port 58 is configured to enable connection of tubing 82 of smoke evacuation tubing assembly 80 thereto to thereby define a flow path from slots 56, through channel 54 and port lumen 59, to tubing 82.

With continued reference to FIGS. 1-3, distal smoke evacuator 60 is configured to releasably engage distal rim 24 of access device 20 and includes a tube ring 62, a connector 64, and a plurality of clips 66. Tube ring 62 defines a generally circular configuration but is interrupted to define opposed open ends 63 that are engaged about or within opposed ends 65a of connector 64 in fluid communication therewith. Tube ring 62 defines a plurality of apertures 68 extending therethrough in communication with an internal lumen 70 defined through tube ring 62. Apertures 68 may be equally-spaced about tube ring 62 and may define similar or different diameters. Apertures 68 are oriented in a distally-facing direction although apertures 68 may additionally or alternatively be oriented in a radially-inward facing direction.

Clips 66 of distal smoke evacuator 60 include first portions 67a configured to engage tube ring 62 and second portions 67b configured to engage distal rim 24 of access device 20. First portions 67a may include apertures configuration receive tube ring 62 therethrough or any other suitable configuration for permanently or releasably engaging tube ring 62. Second portions 67b may include arms configured to snap-fit about distal rim 24 or other suitable configuration for releasably engaging distal rim 24.

Connector 64, as noted above, includes opposed ends 65a configured for receipt of opposed open ends 63 of tube ring 62 in engagement thereabout or therein in fluid communication therewith. Connector 64 further includes a connection port 65b that is configured to enable connection of tubing 84 of smoke evacuation tubing assembly 80 thereto to thereby define a flow path from apertures 68, through internal lumen 70 and connector 64 to tubing 84.

Smoke evacuation tubing assembly 80, as noted above, includes tubing 82 configured to fluidly connect to proximal smoke evacuator 40 and tubing 84 configured to fluidly connect to distal smoke evacuator 60. Smoke evacuation tubing assembly 80 further includes a connector 86 and outflow tubing 89. Connector 86 includes inputs 87a, 87b configured to connect to tubing 82, 84, respectively, and an output 88 configured to connect to outflow tubing 89. Outflow tubing 89, in turn, is configured to connect to a source of suction (not shown) to enable evacuation of smoke through proximal and distal smoke evacuators 40, 60, respectively, via smoke evacuation tubing assembly 80.

Referring generally to FIGS. 1-3, in use, distal smoke evacuator 60 is initially engaged with distal rim 24 of access device 20, e.g., by snapping clips 66 about distal rim 24, and tubing 84 is connected with connection port 65b of connector 64. Thereafter, access device 20, with distal smoke evacuator 60 engaged thereon, is positioned within an opening in tissue "T" such that distal rim 24 is disposed on an internal surface of tissue "T" on the internal side of the opening in tissue "T," body 26 extends through the opening in tissue "T," and proximal rim 22 is disposed on an exterior surface of tissue "T" on the external side of the opening in tissue "T." In this position, tube ring 62 of distal smoke evacuator 60 is disposed distally of proximal rim 22 of access device 20 on the internal side of the opening in tissue "T," surrounding the opening in tissue "T," while tubing 84 extends from distal smoke evacuator 60, through the opening in tissue "T" (externally or internally of access device 20) to the exterior side thereof.

Next, proximal smoke evacuator 40, lead by open distal end 46 thereof, is inserted into passageway 28 of access device 20 and is flexed or otherwise manipulated to permit lip 52 to pass distally through proximal rim 22 into passageway 28. Once proximal smoke evacuator 40 is inserted sufficiently into passageway 28 of access device 20 such that lip 52 is disposed distally of proximal rim 22, proximal smoke evacuator 40 may be released, allowing proximal smoke evacuator 40 to return to or towards its at-rest position, whereby lip 52 is engaged within overhang 29, thereby locking proximal smoke evacuator 40 in engagement within access device 20. Finally, or at any other suitable point, tubing 82 is connected between proximal smoke evacuator 40 and connector 86 and outflow tubing 89 is connected between connector 86 and the source of suction. Accordingly, in use, the source of suction may be activated to evacuate smoke on the internal side of the opening in tissue "T" surrounding the opening in tissue "T," e.g., via apertures 68 of distal smoke evacuator 60, and on the external side of the opening in tissue "T" surrounding the opening in tissue "T," e.g., via slots 56 of proximal smoke evacuator 40. In embodiments, connector 86 includes a valve (not shown) enabling selective control of suction through proximal and distal smoke evacuators 40, 60, respectively, thus enabling selective operation or either or both of proximal and distal smoke evacuators 40, 60, respectively. In embodiments, rather than a common smoke evacuation tubing assembly 80, separate tubing assemblies may be provided for connecting to (and, in embodiments, providing independent control of) of proximal and distal smoke evacuators 40, 60, respectively.

Figure 4:
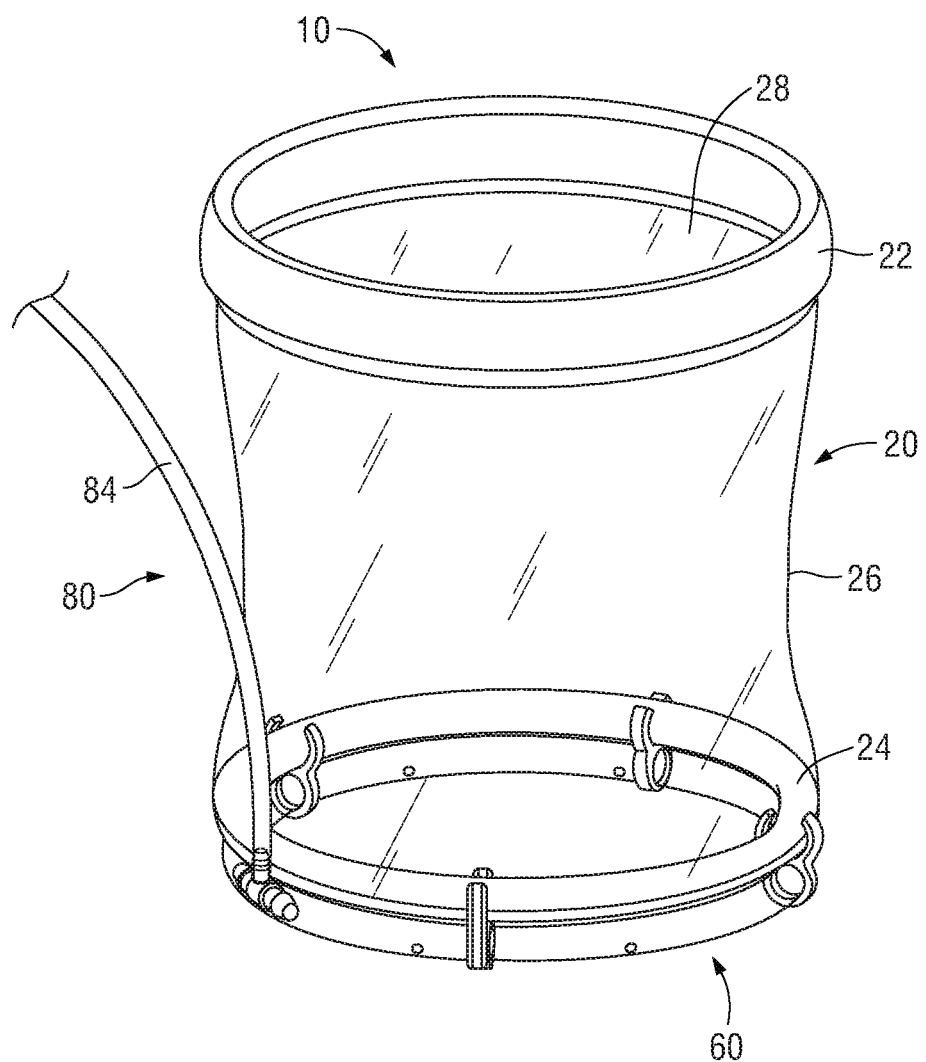
FIG. 4 is a perspective view of the surgical access system of FIG. 1 without the proximal smoke evacuator.

Turning to FIG. 4, in embodiments, surgical access system 10 is provided without a proximal smoke evacuator and, instead, access device 20, distal smoke evacuator 60, and evacuation tubing assembly 80. In such aspects, evacuation tubing assembly 80 may include tubing 84 connected directly between distal smoke evacuator 60 and the source of suction (not shown), although other configurations are also contemplated.

Figure 5A:
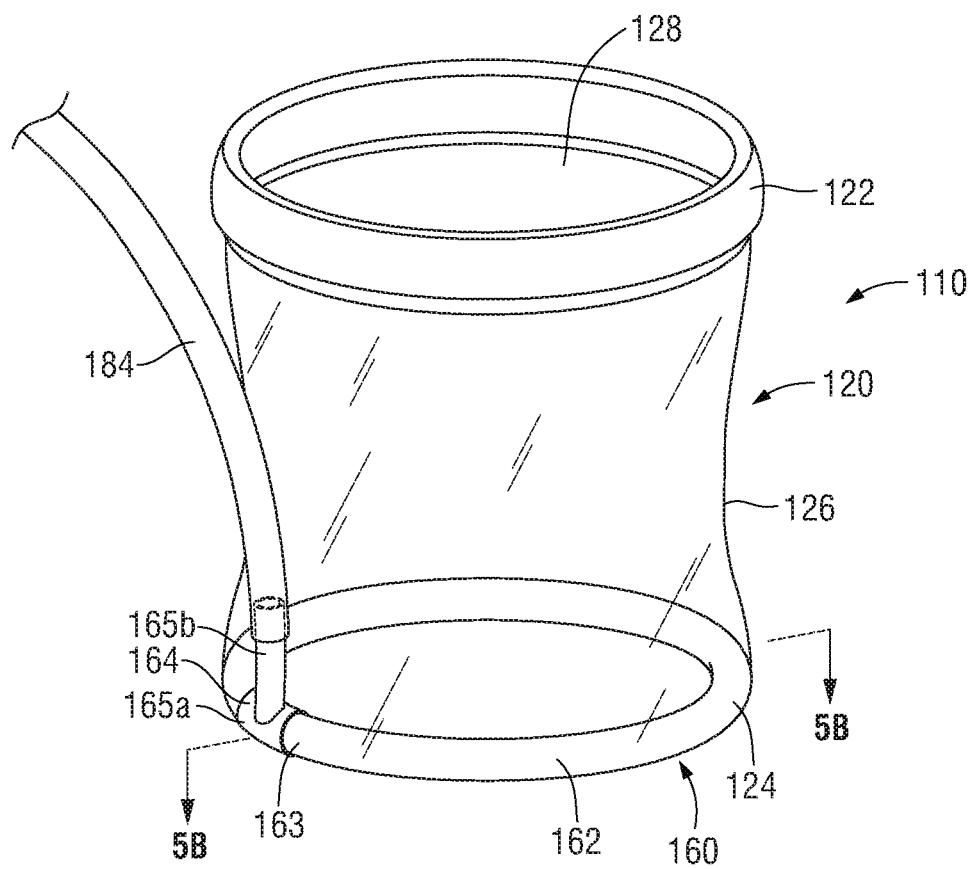
FIG. 5A is a perspective view of another surgical access system provided in accordance with the present disclosure including a surgical access device incorporating a distal smoke evacuator.
Figure 5B:
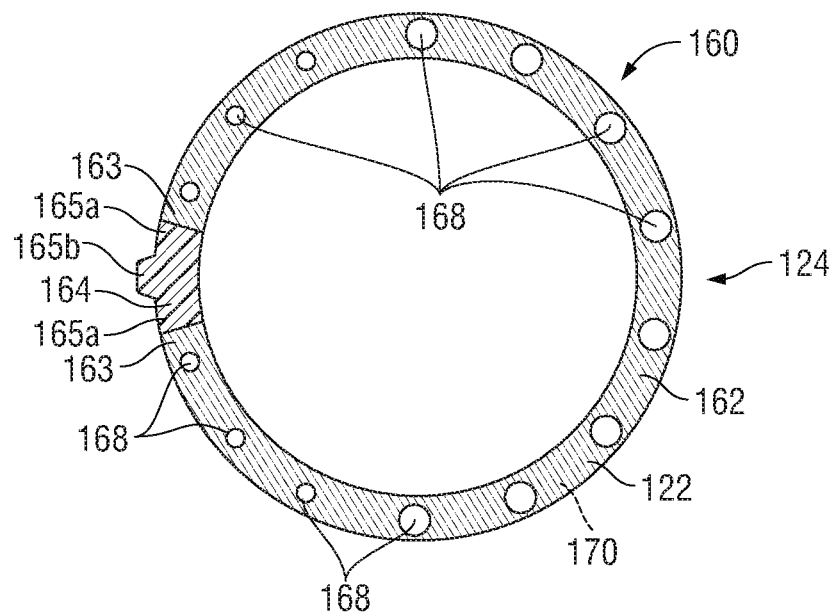
FIG. 5B is a transverse, cross-sectional view taken along section line "5B-5B" of FIG. 5A.

Referring to FIGS. 5A and 5B, another surgical access system provided in accordance with the present disclosure is shown generally identified by reference numeral 110. Surgical access system 110 includes a surgical access device 120 incorporating therein a distal smoke evacuator 160. Surgical access system 110 further includes tubing 184 configured to connect distal smoke evacuator 160 with a source of suction (not shown). Surgical access system 110 may be utilized with or without a proximal smoke evacuator, e.g., proximal smoke evacuator 40 (FIGS. 1-3).

Surgical access device 120 is similar to and may include any of the features of surgical access device 20 (FIGS. 1-3), and vice versa, except as specifically contradicted below. Accordingly, only the differences between surgical access device 120 and surgical access device 20 (FIGS. 1-3) are detailed below while similarities are summarily described or omitted entirely.

Surgical access device 120 includes a proximal rim 122, a distal rim 124, and a body 126 extending between proximal and distal rims 122, 124, respectively. Body 126 defines a longitudinally-extending passageway 128 to permit access to an internal surgical site therethrough. Distal rim 124 of surgical access device 120 incorporates distal smoke evacuator 160 therein. More specifically, distal rim 124 of surgical access device 120 includes a tube ring 162 and a connector 164. Tube ring 162 defines a generally circular configuration but is interrupted to define opposed open ends 163 that are engaged about or within opposed ends 165a of connector 164 in fluid communication therewith. Tube ring 162 defines a plurality of apertures 168 extending therethrough in communication with an internal lumen 170 defined through tube ring 162. Apertures 168 may be equally-spaced about tube ring 162 and may define similar or different diameters. In embodiments, as illustrated (see FIG. 5B), apertures 168 of tube ring 162 define increasing diameters the further the circumferential distance apertures 168 are spaced from connector 164, e.g., balancing the resistance of fluid flow through tube ring 162 to thereby provide substantially equal suction and, thus, smoke evacuation about the circumference of tube ring 162. Apertures 168 are oriented in a distally-facing direction although apertures 168 may additionally or alternatively be oriented in a radially-inward facing direction.

Connector 164, as noted above, includes opposed ends 165a configured for receipt of opposed open ends 163 of tube ring 162 in engagement thereabout or therein in fluid communication therewith. Connector 164 further includes a connection port 165b that is configured to enable connection of tubing 184 thereto to thereby define a flow path from apertures 168, through internal lumen 170 and connector 164 to tubing 184. Connector 164 may be integral with tube ring 162 and/or tubing 184 or may be separable therefrom.

Figure 6A:
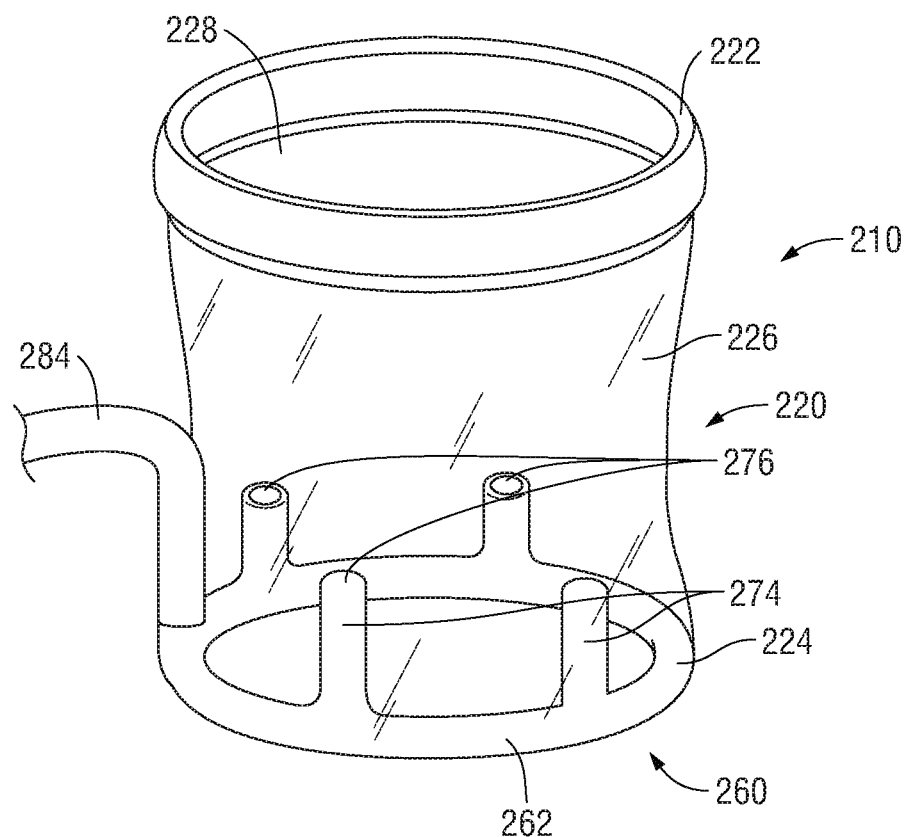
FIG. 6A is a perspective view of still another surgical access system provided in accordance with the present disclosure including a surgical access device incorporating a distal smoke evacuator.
Figure 6B:
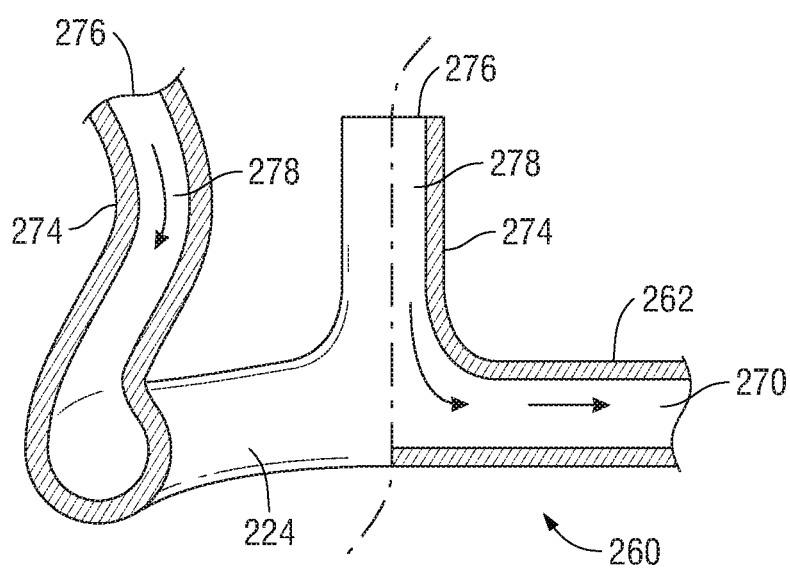
FIG. 6B is an enlarged, partial cross-sectional, partial perspective view of a portion of the distal end of the surgical access system of FIG. 6A.

With reference to FIGS. 6A and 6B, another surgical access system provided in accordance with the present disclosure is shown generally identified by reference numeral 210. Surgical access system 210 includes a surgical access device 220 incorporating therein a distal smoke evacuator 260. Surgical access system 210 further includes tubing 284 configured to connect distal smoke evacuator 260 with a source of suction (not shown). Surgical access system 210 may be utilized with or without a proximal smoke evacuator, e.g., proximal smoke evacuator 40 (FIGS. 1-3).

Surgical access device 220 is similar to and may include any of the features of surgical access devices 20 (FIGS. 1-3), 120 (FIGS. 5A-5B), and vice versa, except as specifically contradicted below. Accordingly, only the differences between surgical access device 120 and surgical access devices 20, 120 (FIGS. 1-3 and 5A-5B, respectively) are detailed below while similarities are summarily described or omitted entirely.

Surgical access device 220 includes a proximal rim 222, a distal rim 224, and a body 226 extending between proximal and distal rims 222, 224, respectively. Body 226 defines a longitudinally-extending passageway 228 to permit access to an internal surgical site therethrough. Distal rim 224 of surgical access device 220 incorporates distal smoke evacuator 260 therein. More specifically, distal rim 224 of surgical access device 220 includes a tube ring 262 defining a generally circular configuration with an internal lumen 270 extending therethrough. Tube ring 262 further includes a plurality of fingers 274 extending proximally therefrom on an interior side of body 226 of surgical access device 220, e.g., within passageway 228. Fingers 274 define proximally-facing open free ends 276 and lumens 278 extending therethrough that establish fluid communication between open free ends 276 and internal lumen 270 of tube ring 262.

A connector 264 of distal smoke evacuator 260 is integral with or separate from tube ring 262 and is configured to fluidly couple internal lumen 270 of tube ring 262 with tubing 284 to thereby define a flow path from open free ends 276 of fingers 274, through lumens 278, internal lumen 170, and connector 264 to tubing 284.

As an alternative to distal smoke evacuator 260 being incorporated into distal rim 224, distal rim 224 may be configured similar to distal rim 24 (FIGS. 1-3) and distal smoke evacuator 260 may be configured to releasably engage distal rim 224, similarly as detailed above with respect to surgical access system 10 (FIGS. 1-3).

From the foregoing and with reference to the various drawings, those skilled in the art will appreciate that certain modifications can be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical access system, comprising:
   an access device including a proximal rim configured for positioning on an external side of an opening in tissue, a distal rim configured for positioning on an internal side of an opening in tissue, and a body interconnecting the proximal and distal rims, the body configured to extend through an opening in tissue and defining a passageway extending therethrough for insertion of a surgical instrument through the opening in tissue into an internal surgical site; and
   a distal smoke evacuator integrated into or coupled to the distal rim, the distal smoke evacuator including a tube ring adapted to connect to a source of suction to evacuate smoke circumferentially about an internal side of an opening in tissue, wherein the tube ring defines an internal lumen and a plurality of apertures communicating with the internal lumen, wherein the distal smoke evacuator is configured to evacuate smoke through the plurality of apertures into the internal lumen and wherein the plurality of apertures is defined on a distally-facing side of the tube ring.

2. The surgical access system according to claim 1, wherein the plurality of apertures includes apertures of different diameters to provide substantially equal smoke evacuation about the tube ring.

3. The surgical access system according to claim 1, wherein the distal smoke evacuator further includes a connector and tubing, the connector configured to fluidly couple to the tubing to enable smoke evacuation from the tube ring, through the connector, to the tubing.

4. The surgical access system according to claim 1, wherein the distal smoke evacuator further includes a plurality of fingers extending proximally from the tube ring, each finger of the plurality of fingers defining an open end and a lumen communicating with an internal lumen of the tube ring, wherein the distal smoke evacuator is configured to evacuate smoke through the open ends of the fingers and into the internal lumen.

5. The surgical access system according to claim 4, wherein the open ends of the fingers are proximally-facing.

6. The surgical access system according to claim 1, wherein the tube ring defines the distal rim of the access device.

7. The surgical access system according to claim 1, wherein the tube ring is releasably engaged with the distal rim of the access device.

8. The surgical access system according to claim 7, wherein the distal smoke evacuator includes a plurality of clips engaged with the tube ring and configured to releasably engage the distal rim to thereby releasably engage the tube ring with the distal rim.

9. The surgical access system according to claim 1, further comprising a proximal smoke evacuator configured to engage the proximal rim, the proximal smoke evacuator configured to evacuate smoke circumferentially about an external side of an opening in tissue.

10. The surgical access system according to claim 9, wherein the proximal smoke evacuator includes a tissue guard body.

11. The surgical access system according to claim 9, wherein the proximal smoke evacuator includes a lip configured to releasably engage an overhang defined by the proximal rim to releasably engage the proximal smoke evacuator with the proximal rim within the passageway.

12. The surgical access system according to claim 9, further comprising a smoke evacuation tubing assembly including:
a first tubing coupled to the proximal smoke evacuator;
a second tubing coupled to the distal smoke evacuator;
a connector connecting the first and second tubings; and
an outflow tubing connected to the connector, the outflow tubing adapted to connect to a source of suction for evacuating smoke through proximal and distal smoke evacuators via the first and second tubings, respectively.

13. A surgical access system, comprising:
an access device including a proximal portion configured for positioning on an external side of an opening in tissue, a distal portion configured for positioning on an internal side of an opening in tissue, and a body portion interconnecting the proximal and distal portions, the body portion configured to extend through an opening in tissue and defining a passageway extending therethrough for insertion of a surgical instrument through the opening in tissue into an internal surgical site;
a distal smoke evacuator disposed at the distal portion of the access device, the distal smoke evacuator including a tube ring defining an internal lumen and a plurality of fluid paths in communication with the internal lumen; and
tubing coupled to the distal smoke evacuator in fluid communication with the internal lumen, the tubing adapted to connect to a source of suction to evacuate smoke from an internal side of an opening in tissue, wherein the access device includes a distal rim disposed at the distal portion thereof, and wherein the tube ring is releasably engaged with the distal rim.

14. The surgical access assembly according to claim 13, wherein the tube ring defines a distal rim of the access device.

15. The surgical access system according to claim 13, wherein the tube ring defines a plurality of apertures defining the plurality of fluid paths.

16. The surgical access system according to claim 13, wherein the tube ring includes a plurality of fingers extending proximally from the tube ring, each finger of the plurality of fingers defining an open end and a lumen, the open ends and lumens cooperating to define the plurality of fluid paths.

17. The surgical access system according to claim 13, further comprising a proximal smoke evacuator configured to engage the proximal portion of the access device, wherein the tubing is further configured to connect to the proximal smoke evacuator to evacuate smoke from an external side of an opening in tissue.

18. A surgical access system, comprising:
an access device including a proximal rim configured for positioning on an external side of an opening in tissue, a distal rim configured for positioning on an internal side of an opening in tissue, and a body interconnecting the proximal and distal rims, the body configured to extend through an opening in tissue and defining a passageway extending therethrough for insertion of a surgical instrument through the opening in tissue into an internal surgical site; and
a distal smoke evacuator integrated into or coupled to the distal rim, the distal smoke evacuator including a tube ring adapted to connect to a source of suction to evacuate smoke circumferentially about an internal side of an opening in tissue, wherein the distal smoke evacuator further includes a plurality of fingers extending proximally from the tube ring, each finger of the plurality of fingers defining an open end and a lumen communicating with an internal lumen of the tube ring, wherein the distal smoke evacuator is configured to evacuate smoke through the open ends of the fingers and into the internal lumen.

\* \* \* \* \*